United States Patent
Kamo et al.

(10) Patent No.: US 9,700,920 B2
(45) Date of Patent: Jul. 11, 2017

(54) CLEANING TOOL FOR COLLECTION MEMBER, PARTICLE DETECTOR, AND MANUFACTURING METHOD FOR CLEANING TOOL FOR COLLECTION MEMBER

(71) Applicant: Sharp Kabushiki Kaisha, Osaka-shi, Osaka (JP)

(72) Inventors: Tomonori Kamo, Osaka (JP); Hideaki Fujita, Osaka (JP); Kazushi Fujioka, Osaka (JP); Hiroki Okuno, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 371 days.

(21) Appl. No.: 14/410,123

(22) PCT Filed: Jun. 26, 2013

(86) PCT No.: PCT/JP2013/067487
§ 371 (c)(1),
(2) Date: Dec. 22, 2014

(87) PCT Pub. No.: WO2014/003048
PCT Pub. Date: Jan. 3, 2014

(65) Prior Publication Data
US 2015/0321227 A1 Nov. 12, 2015

(30) Foreign Application Priority Data
Jun. 29, 2012 (JP) .................... 2012-147181

(51) Int. Cl.
*B08B 1/00* (2006.01)
*A46B 3/02* (2006.01)
(Continued)

(52) U.S. Cl.
CPC ............. *B08B 1/002* (2013.01); *A46B 3/02* (2013.01); *A46B 3/08* (2013.01); *A46D 3/04* (2013.01);
(Continued)

(58) Field of Classification Search
CPC .... A46B 3/00; A46B 3/02; A46B 3/04; A46B 3/06; A46B 3/08; A46B 3/10; A46B 3/12;
(Continued)

(56) References Cited

U.S. PATENT DOCUMENTS

| 134,745 | A | * | 1/1873 | Gorman | ............... A46B 3/08 15/177 |
| 828,540 | A | * | 8/1906 | De Vere | ............... A46B 3/08 15/177 |

(Continued)

FOREIGN PATENT DOCUMENTS

| DE | 2505198 | * | 8/1975 |
| FR | 2 599 951 A1 | | 12/1987 |

(Continued)

OTHER PUBLICATIONS

Official Communication issued in International Patent Application No. PCT/JP2013/067487, mailed on Sep. 17, 2013.

*Primary Examiner* — Mark Spisich
(74) *Attorney, Agent, or Firm* — Keating & Bennett, LLP

(57) ABSTRACT

A cleaning tool for a collection member includes a brush unit and a mount portion. The brush unit includes a bristle and a woven portion into which a root of the bristle is woven so as to be held by the woven portion. The mount portion includes a placement surface on which the woven portion is placed and a securing portion to which the brush unit is bonded. In the cleaning tool for the collection member, the woven portion includes two first outer surfaces that are located at respective ends of the placement surface and that
(Continued)

extend parallel to a direction in which the bristle extends. In the cleaning tool for the collection member, the brush unit is secured to the mount portion by bonding a region that includes at least part of each of the two first outer surfaces to the securing portion with an adhesive.

8 Claims, 14 Drawing Sheets

(51) Int. Cl.
    *A46B 3/08* (2006.01)
    *A46B 3/04* (2006.01)
    *G01N 15/00* (2006.01)
    *G01N 21/00* (2006.01)
    *A46D 3/04* (2006.01)
    *G01N 21/64* (2006.01)
    *G01N 15/14* (2006.01)
    *G01N 15/06* (2006.01)

(52) U.S. Cl.
    CPC ..... *G01N 15/0612* (2013.01); *G01N 15/1434* (2013.01); *G01N 21/6486* (2013.01); *A46B 2200/405* (2013.01); *G01N 2015/0065* (2013.01); *G01N 2201/06113* (2013.01)

(58) Field of Classification Search
CPC .. A46B 3/16; A46B 3/18; B08B 1/002; B08B 2240/00
USPC ...... 15/191.1, 192, 193, 195, 196, 199, 171, 15/177, 246, 246.5
See application file for complete search history.

(56) References Cited

U.S. PATENT DOCUMENTS

| | | | |
|---|---|---|---|
| 930,375 A * | 8/1909 | Hascy | A46B 15/00 15/192 |
| 1,509,417 A * | 9/1924 | Caldwell | A46B 3/08 15/177 |
| 2005/0247868 A1 | 11/2005 | Call et al. | |
| 2012/0154348 A1 | 6/2012 | Okuno | |

FOREIGN PATENT DOCUMENTS

| | | | |
|---|---|---|---|
| JP | 3-125081 | * | 5/1991 |
| JP | 10-023927 A | | 1/1998 |
| JP | 2002-306246 A | | 10/2002 |
| JP | 2004-077920 A | | 3/2004 |
| JP | 2006-296496 | * | 11/2006 |
| JP | 2007-526478 A | | 9/2007 |
| WO | 2012/081284 A1 | | 6/2012 |

* cited by examiner

CONCENTRATION N OF BIOLOGICAL PARTICLES (PARTICLES/m³)

CLEANING TOOL FOR COLLECTION MEMBER, PARTICLE DETECTOR, AND MANUFACTURING METHOD FOR CLEANING TOOL FOR COLLECTION MEMBER

TECHNICAL FIELD

The present invention relates to a cleaning tool for a collection member, a particle detector, and a manufacturing method for the cleaning tool for the collection member. The present invention particularly relates to a cleaning tool for the collection member, a particle detector, and a manufacturing method for the cleaning tool for the collection member in which removal of the bristles can be prevented and with which the reliability of measurement can be improved.

BACKGROUND ART

In order to reduce the frequency of replacement of a collection member of a particle detector and in order to reduce the cost for particle detection, a cleaning tool that removes minute foreign substances attracted to the collection member uses a brush member.

Although it is a brush member used not for a particle detector but for an electrophotographic device, examples of the related-art brush member include a brush member described in Japanese Unexamined Patent Application Publication No. 2004-77920 (PTL 1).

The brush member described in PTL 1 is formed by arranging a plurality of chemical-fiber bristles parallel to one another, holding root portions of the bristles by chemical-fiber holding threads extending in a direction intersecting a direction in which the bristles extend, and napping the tips of the bristles. The tips of the bristles of the brush member are brought into contact with a component to be cleaned during use in the electrophotographic device. By applying an ultrasonic wave or a high frequency to the bristles and the holding threads, the bristles and the holding threads are fused and heat welded to one another.

Japanese Unexamined Patent Application Publication No. 10-23927 (PTL 2) describes a brush member for an electrophotographic device as follows: that is, an electrically conductive brush includes a plurality of electrically conductive bristles arranged parallel to one another and a holding portion that holds the bristles on one side of the bristles. The lengths of the bristles of the electrically conductive brush on end portion sides are shorter than those in the other portions.

CITATION LIST

Patent Literature

PTL 1: Japanese Unexamined Patent Application Publication No. 2004-77920
PTL 2: Japanese Unexamined Patent Application Publication No. 10-23927

SUMMARY OF INVENTION

Technical Problem

By using a generally supplied reeled brush material whose root portions of the bristles are held by a simple woven structure, a cleaning unit that removes minute foreign substances attracted to a collection member can be realized at a low cost.

However, when individual brush members are formed by cutting the reeled brush material, the cut portions of the woven structure become loose, and accordingly, the bristles are easily removed. When the bristle removed from the cleaning unit is attracted to a measuring surface of a substrate during drive of a particle detector, it is difficult to obtain reliable measurement results.

In the brush member described in PTL 1, the bristles and the holding threads are welded to one another by applying an ultrasonic wave or a high frequency thereto in order to prevent the tips of the bristles from being bonded by the adhesive. In this case, the precondition is totally different from that of the present invention, in which the precondition is that the bristles are bonded to a securing member with an adhesive as will be described later.

In the brush member described in PTL 2, removal of the bristles is prevented by reducing the lengths of the bristles disposed at the end portions of the brush member, where holding forces are low. Thus, removal of the bristles is prevented with a structure totally different from that of the present invention.

The present invention is proposed in view of the above-described problem, and an object of the present invention is to provide a cleaning tool for a collection member, a particle detector, and a manufacturing method for the cleaning tool for the collection member in which removal of the bristles can be prevented and with which the reliability of measurement can be improved.

Solution to Problem

According to the present invention, a cleaning tool for a collection member that cleans a collection member of a particle detector includes a brush unit and a mount portion. The brush unit includes a bristle and a woven portion into which a root of the bristle is woven so as to be held by the woven portion. The mount portion includes a placement surface on which the woven portion is placed and a securing portion to which the brush unit is bonded. In the cleaning tool for the collection member, the woven portion includes two first outer surfaces that are located at respective ends of the placement surface and that extend parallel to a direction in which the bristle extends. In the cleaning tool for the collection member, the brush unit is secured to the mount portion by bonding a region that includes at least part of each of the two first outer surfaces to the securing portion with an adhesive.

In one embodiment, in the above-described cleaning tool for the collection member, the mount portion includes a bonding portion that includes the placement surface. The mount portion also includes a first projecting portion that projects from the placement surface and that is in contact with the bristle. A step is formed between the bonding portion and the first projecting portion.

In one embodiment, in the above-described cleaning tool for the collection member, a gap is formed between the first projecting portion and the woven portion.

In one embodiment, in the above-described cleaning tool for the collection member, the woven portion further includes a second outer surface that opposes an outer surface from which the bristle projects. In addition to the two first outer surfaces, the second outer surface is bonded to the securing portion.

In one embodiment, the above-described cleaning tool for the collection member further includes a pressing plate that opposes the bonding portion and the first projecting portion. The pressing plate together with the mount portion pinches the brush unit.

In one embodiment, in the above-described cleaning tool for the collection member, the mount portion further includes second projecting portions that project further to the bristle side than the first projecting portion at both ends of the first projecting portion. The second projecting portions are in contact with the pressing plate.

According to the present invention, a particle detector includes the above-described cleaning tool for the collection member.

In one embodiment, in the above-described particle detector, after heating of the collection member has been performed, the collection member is cleaned by the brush unit.

According to the present invention, a manufacturing method for a cleaning tool for a collection member that cleans a collection member of a particle detector includes the following steps: preparing a brush strip that includes a bristle and a woven portion into which a root of the bristle is woven so as to be held by the woven portion; forming a brush unit by cutting the strip so that a cut surface is formed in a direction perpendicular to a direction in which the strip extends; placing the brush unit on a mount portion; applying an adhesive at least part of the cut surface of the brush unit; and bonding the cut surface to the mount portion by curing the adhesive.

In one embodiment, the above-described manufacturing method for the cleaning tool for the collection member further includes the step of providing a pressing plate that, together with the mount portion, pinches part of the bristle.

Advantageous Effects of Invention

According to the present invention, it is possible to provide the cleaning tool for the collection member, the particle detector, and the manufacturing method for the cleaning tool for the collection member in which removal of the bristles can be prevented and with which the reliability of measurement can be improved.

DESCRIPTION OF EMBODIMENTS

Embodiments of the present invention will be described below. The same or corresponding elements may be denoted by the same reference signs and repeated description thereof may be omitted.

Unless otherwise described, the scope of the present invention is not necessarily limited to the numbers, quantities, and the like referred in the following embodiments. Also in the following embodiments, unless otherwise described, elements described are not necessarily required in the present invention.

[Principle of Detection of Biological Particles]

A particle detector according to the embodiments 1 and 2, which will be described later, detects biological particles such as pollen, microorganisms, and molds. The principle of detecting biological particles using the particle detector is initially described.

Figure 1:
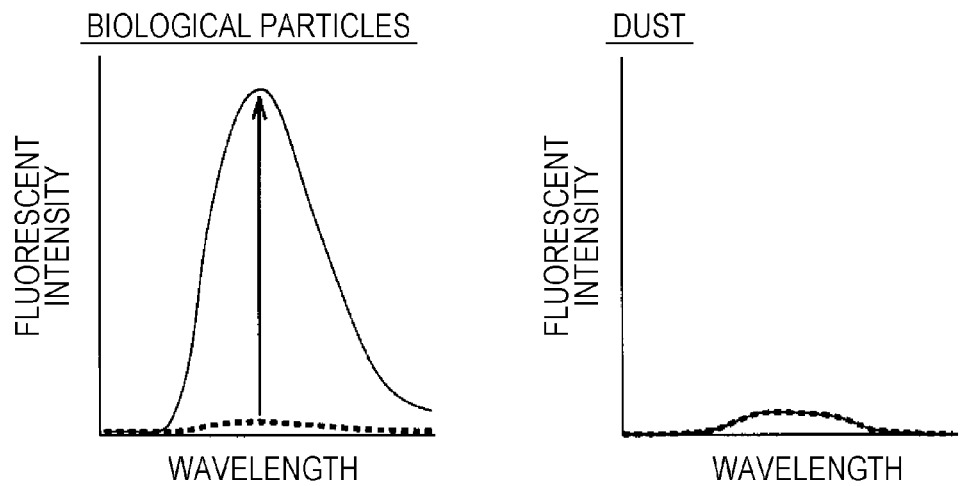
FIG. 1 includes graphs illustrating a change in fluorescent intensity of biological particles before and after heating and a change in fluorescent intensity of dust before and after heating.

FIG. 1 includes graphs illustrating a change in fluorescent intensity of biological particles before and after heating and a change in fluorescent intensity of dust before and after heating.

Airborne biological particles emit fluorescence when being irradiated with ultraviolet light or blue light. In air, however, other particles such as lint of chemical fiber (also referred to as dust hereafter), which emit fluorescence similarly to biological particles, are also suspended. Thus, only by detecting fluorescence, it is impossible to distinguish whether the fluorescence comes from biological particles or dust.

When, as illustrated in FIG. 1, biological particles and dust are heated and changes in the fluorescent intensities (amount of fluorescence) thereof are measured before and after heating, the fluorescent intensity emitted from the dust is not changed by heating and the fluorescent intensity emitted from the biological particles is increased by heating. The particle detector according to the present embodiments measure the fluorescent intensity of a mixed particle of biological particles and dust before and after heating, and obtain the difference between the fluorescent intensity before and after the heating, thereby determining the number of the biological particles.

Figure 2:
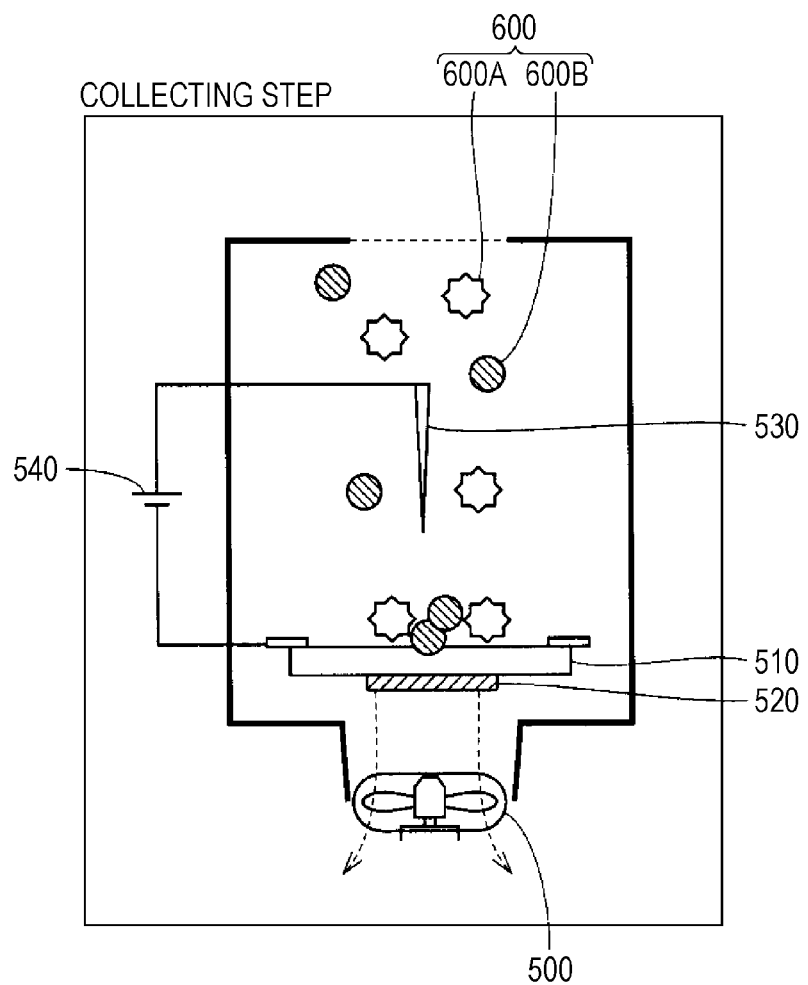
FIG. 2 illustrates a collecting step in biological particle detection.

FIGS. 2 to 6 illustrate steps of detecting biological particles. Referring to FIG. 2, particles are initially collected on a collection substrate 510 (collecting step).

In this step, the collection substrate 510 is disposed opposite an electrostatic stylus 530 and a potential difference is generated between the collection substrate 510 and the electrostatic stylus 530. When air is introduced toward the collection substrate 510 by driving a fan 500, airborne particles 600 around the electrostatic stylus 530 are charged. The charged particles 600 are attracted to a surface of the collection substrate 510 by electrostatic forces. The particles 600 collected on the collection substrate 510 include biological particles 600A and dust 600B including, for example, lint of chemical fiber.

Figure 3:
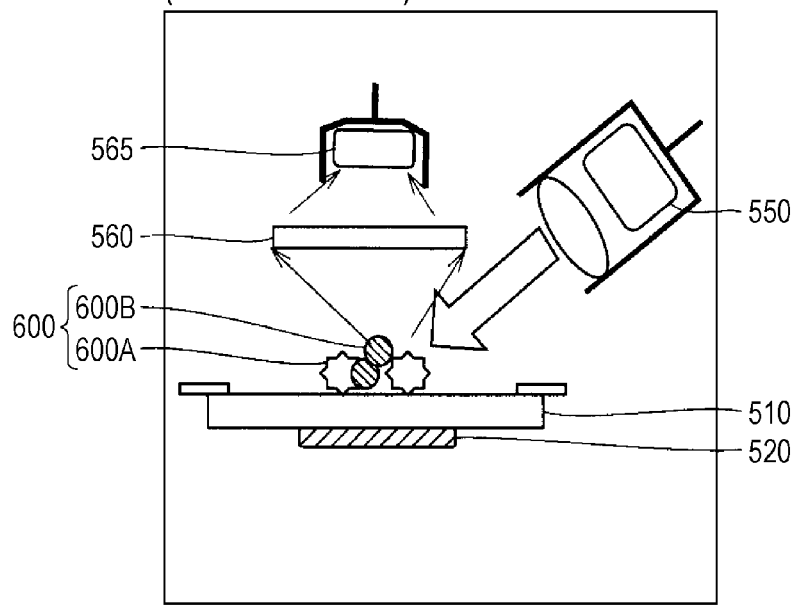
FIG. 3 illustrates a fluorescence measuring step (before heating) in the biological particle detection.

Next, referring to FIG. 3, the intensity of fluorescence emitted from the particles 600 before heating is measured (fluorescence measuring step (before heating)). In this step, the particles 600 collected on the collection substrate 510 is irradiated with excitation light emitted thereto from a light emitting element 550 such as a semiconductor laser, and fluorescence emitted from the particles 600 is received by a light receiving element 565 through a lens 560.

Figure 4:
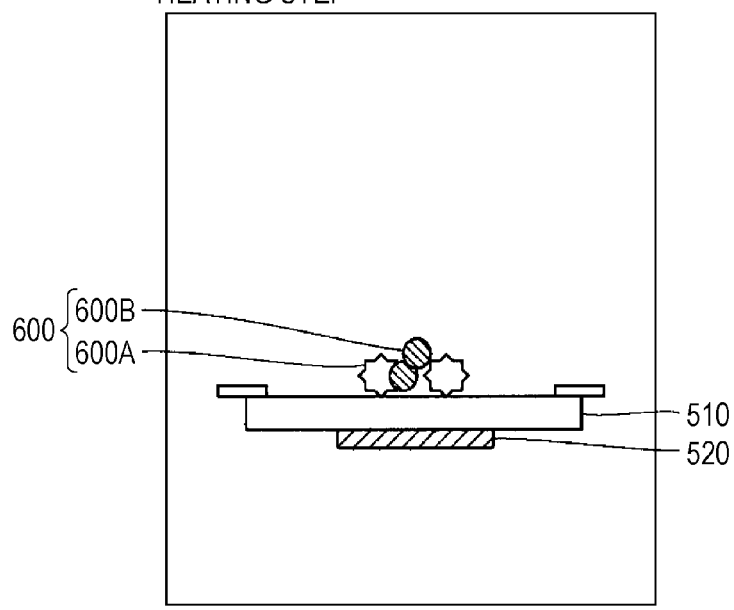
FIG. 4 illustrates a heating step in the biological particle detection.

Next, referring to FIG. 4, the particles 600 collected on the collection substrate 510 is heated by using a heater 520. After the particles 600 have been heated, the collection substrate 510 is cooled (heating step).

Figure 5:
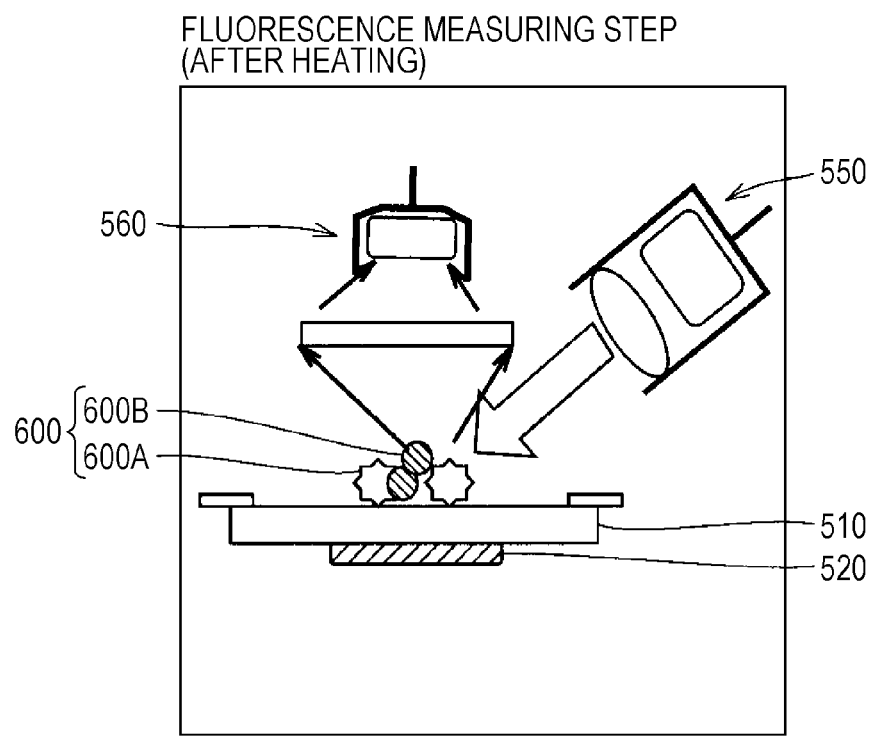
FIG. 5 illustrates a fluorescence measuring step (after heating) in the biological particle detection.

Referring to FIG. 5, next, the intensity of fluorescence emitted from the particles 600 after heating is measured (fluorescence measuring step (after heating)). As has been described, the intensity of fluorescence emitted from the dust 600B is not changed by heating, and the intensity of fluorescence emitted from the biological particles 600A is increased by heating. Thus, the fluorescent intensity measured in this step is greater than that measured in the fluorescence measuring step (before heating) illustrated in FIG. 3.

Figure 7:
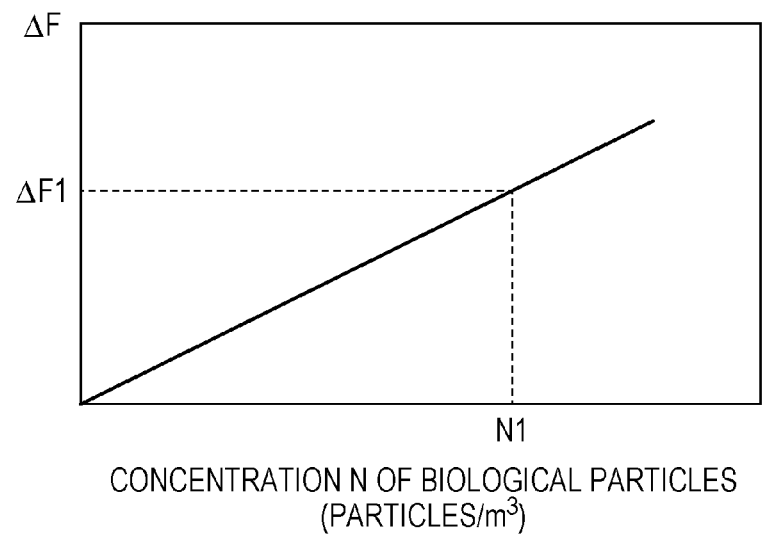
FIG. 7 is a graph illustrating the relationship between an increase ΔF in the fluorescent intensity before and after heating and the concentration of biological particles.

FIG. 7 is a graph illustrating the relationship between an increase ΔF in the fluorescent intensity before and after heating and the concentration of biological particles. Referring to FIG. 7, an increase ΔF1 in the fluorescent intensity is calculated from the difference in the fluorescent intensity before and after heating. A concentration N1 of biological particles corresponding to the calculated increase ΔF1 is found in accordance with a prepared relationship between the increase ΔF in the fluorescent intensity and the concentration N of biological particles. The correspondence relationship between the increase ΔF and the concentration N of biological particles is experimentally predetermined.

Figure 6:
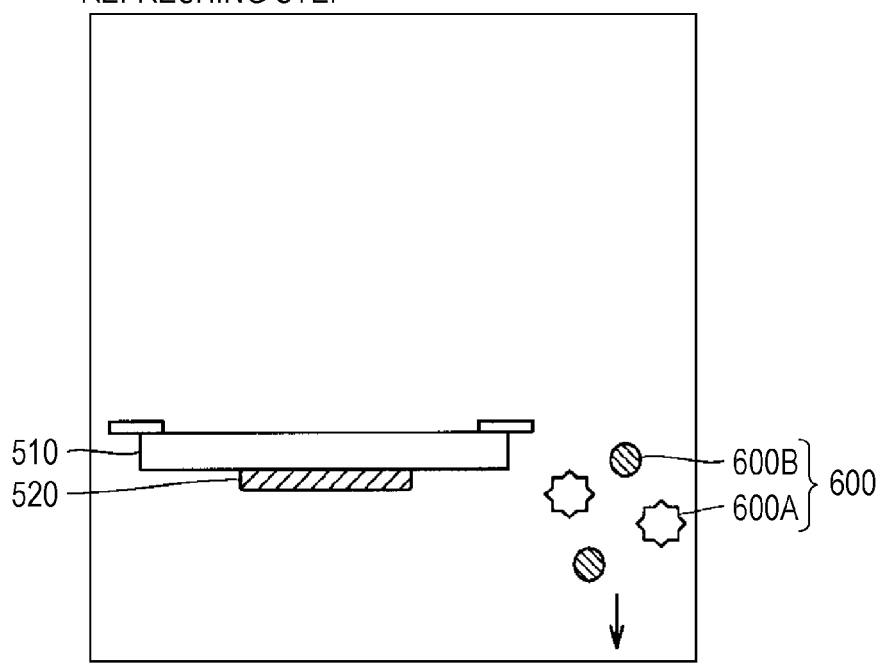
FIG. 6 illustrates a refreshing step in the biological particle detection.

Referring to FIG. 6, next, when detection of the biological particles of the particles 600 has been performed, the particles 600 are removed from the collection substrate 510 (refreshing step).

[General Structure of Particle Detector]

Figure 8:
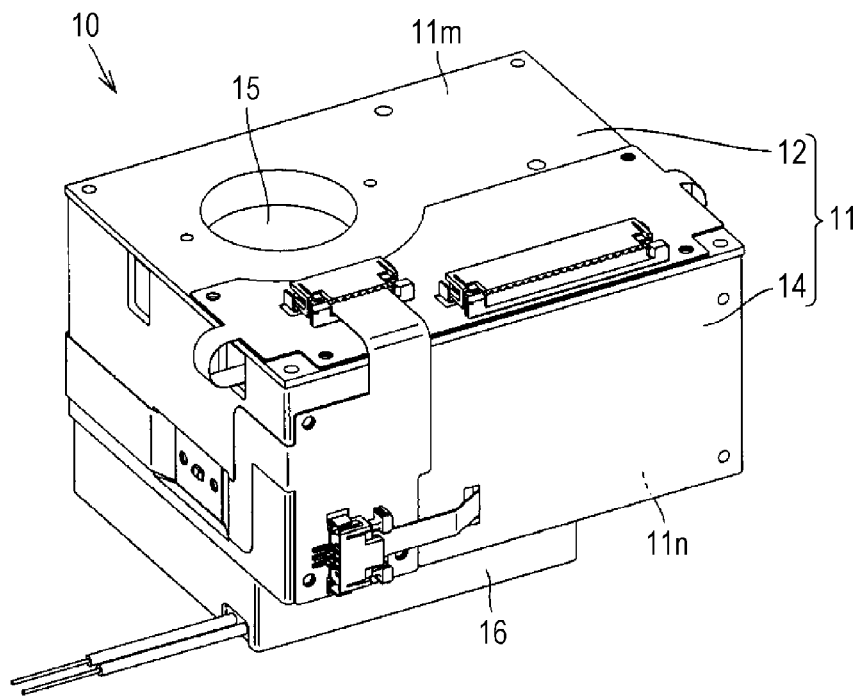
FIG. 8 is a perspective view illustrating the appearance of a particle detector.
Figure 9:
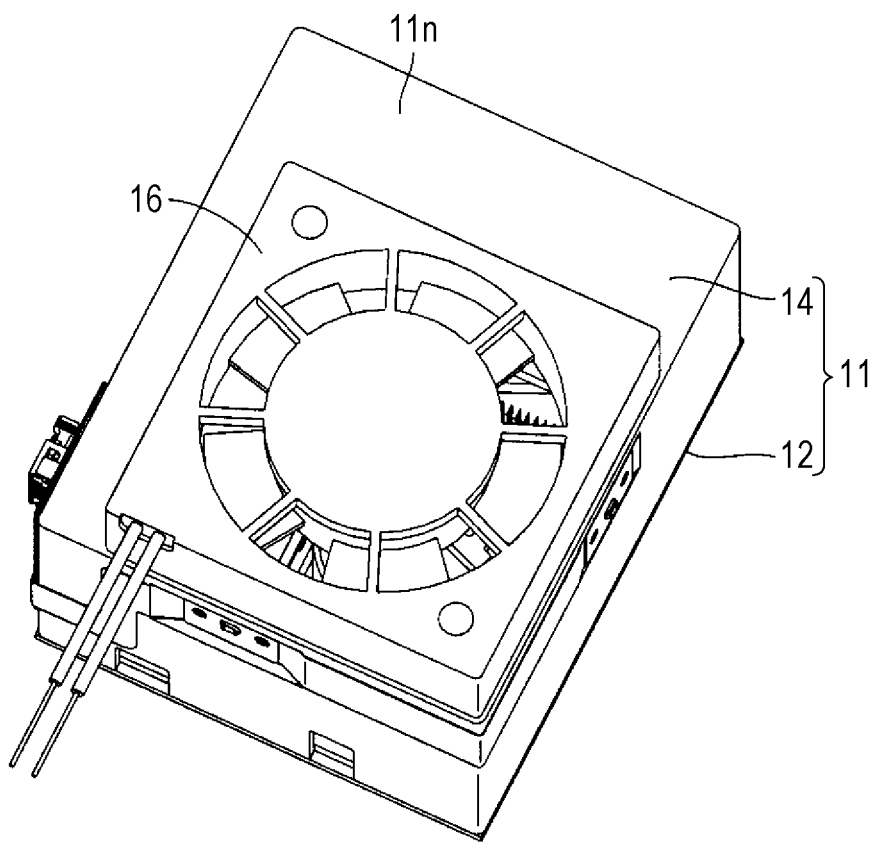
FIG. 9 is another perspective view illustrating the appearance of the particle detector illustrated in FIG. 8.
Figure 10:
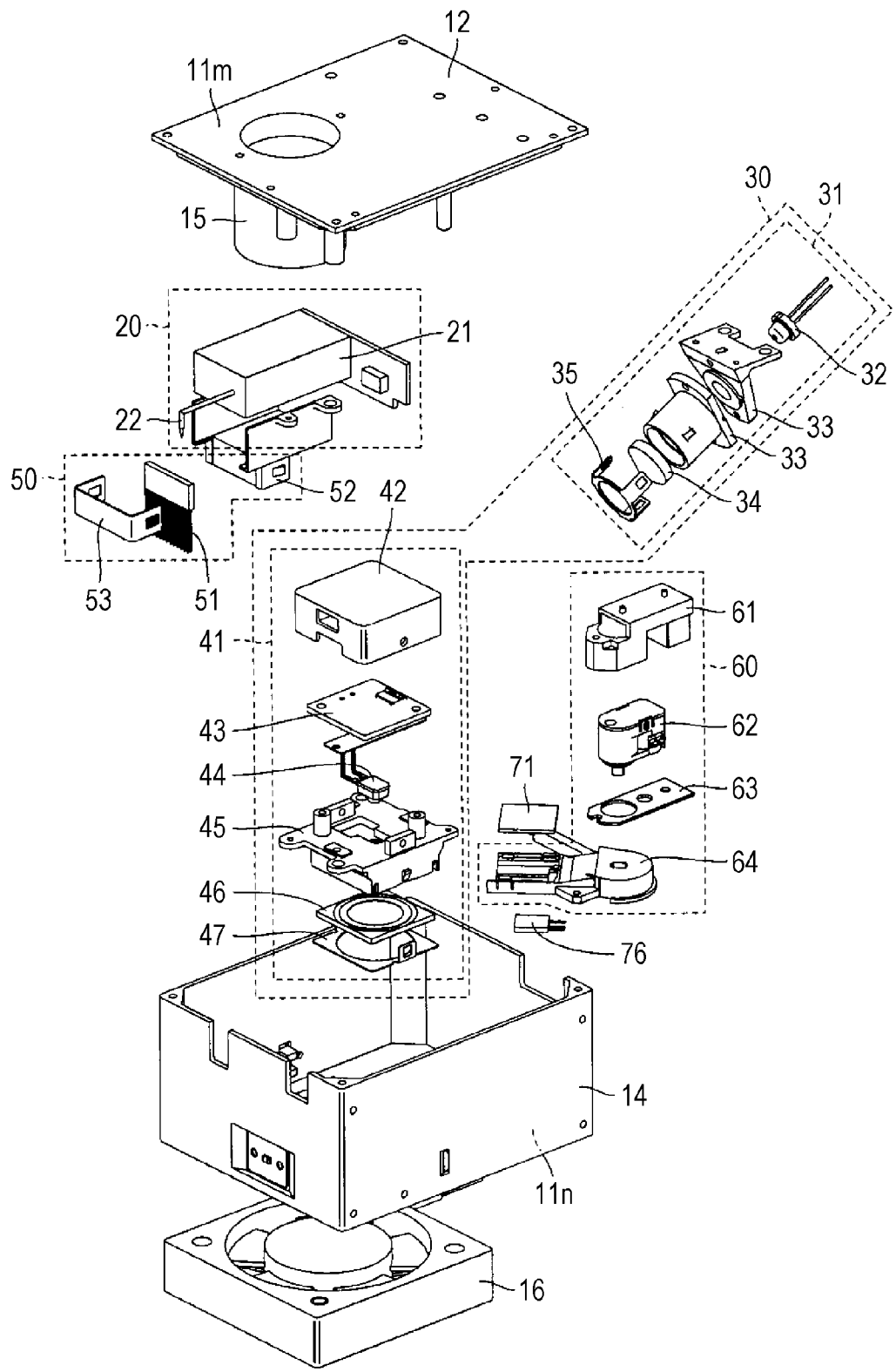
FIG. 10 is an exploded view of the particle detector illustrated in FIG. 8.
Figure 11:
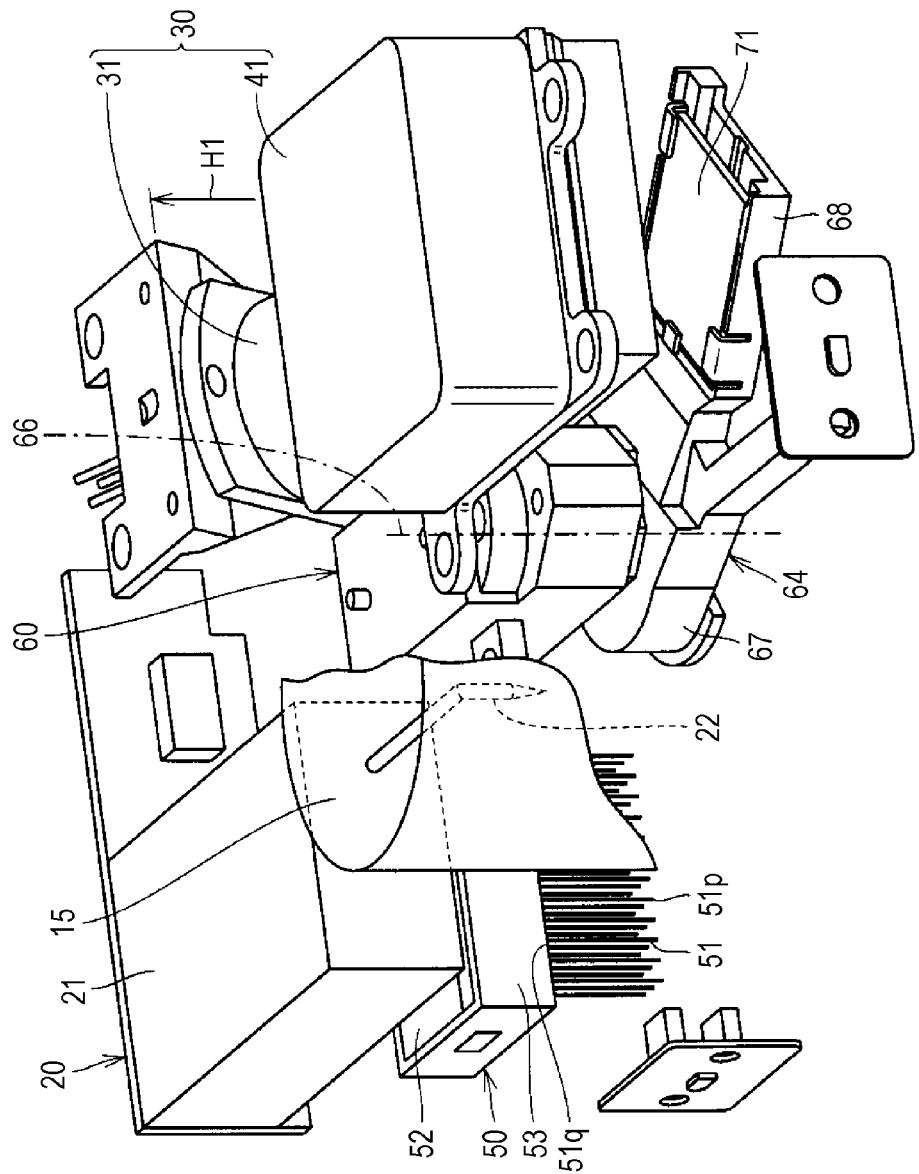
FIG. 11 is a perspective view illustrating an internal structure of the particle detector illustrated in FIG. 8.

FIG. 8 is a perspective view illustrating the appearance of the particle detector. FIG. 9 is another perspective view illustrating the appearance of the particle detector illustrated in FIG. 8. FIG. 10 is an exploded view of the particle detector illustrated in FIG. 8. FIG. 11 is a perspective view illustrating an internal structure of the particle detector illustrated in FIG. 8.

Referring to FIGS. 8 to 11, a particle detector 10 includes a cabinet 11 serving as a housing, a fan 16, a collection unit 20, a fluorescence detection unit 30, and a cleaning unit 50.

The cabinet 11 has a substantially rectangular parallelepiped shape and houses the collection unit 20, the fluorescence detection unit 30, and the cleaning unit 50. In the present embodiments, the cabinet 11 includes an upper cabinet 12 serving as a first housing and a lower cabinet 14 serving as a second housing. The lower cabinet 14 has a box shape having an opening on one side. The upper cabinet 12 has a flat-plate shape that closes the opening of the lower cabinet 14. As an example, the dimensions of the cabinet 11 are 60 mm×50 mm (length and width of the upper cabinet 12)×30 mm (height).

The cabinet 11 has side surfaces 11m and 11n, which oppose each other. The side surface 11m is formed in the upper cabinet 12 and the side surface 11n is formed in the lower cabinet 14.

The cabinet 11 has a collection barrel 15 serving as a barrel-shaped member, which is integrally formed with the cabinet 11. The collection barrel 15 opens at the side surface 11m and extends so as to form a cylindrical shape from the side surface 11m toward the side surface 11n. The collection barrel 15 surrounds an electrostatic stylus 22, which will be described later. Air that includes particles is guided toward a collection substrate 71, which is positioned so as to oppose the electrostatic stylus 22, through the collection barrel 15.

Figure 12:
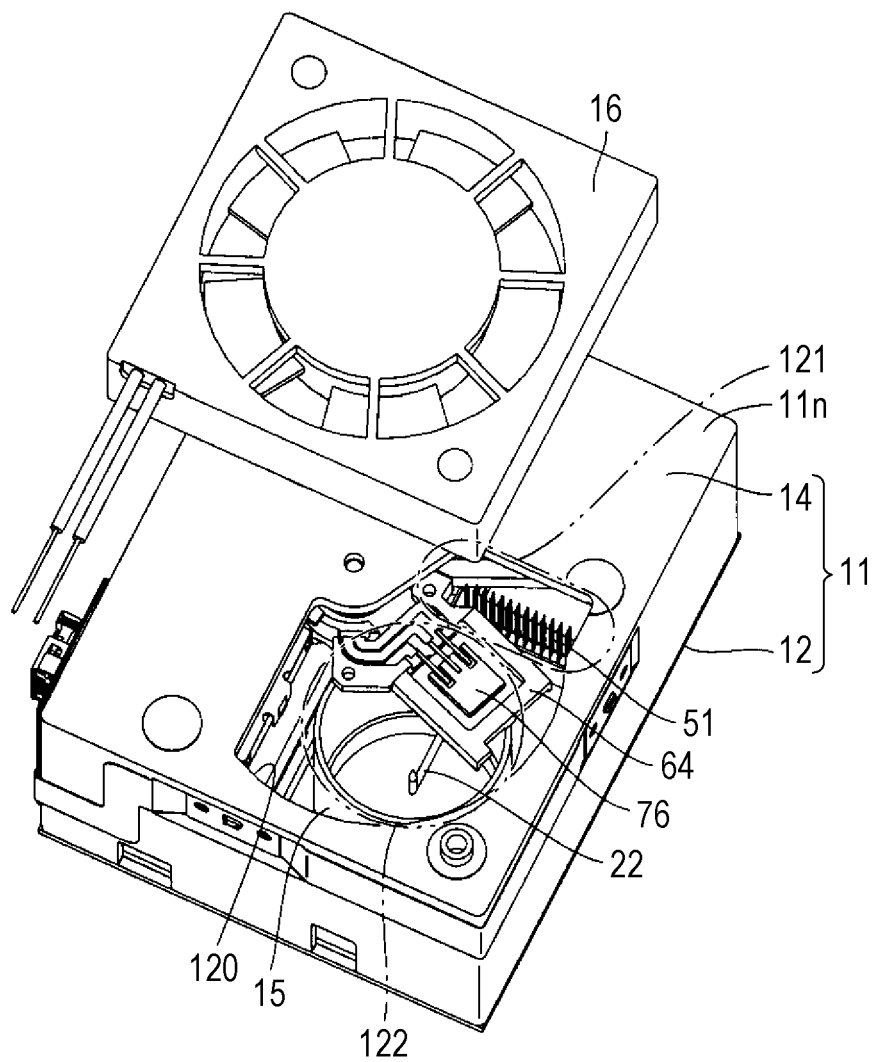
FIG. 12 is a perspective view illustrating the particle detector illustrated in FIG. 9 with a fan detached.

FIG. 12 is a perspective view illustrating the particle detector illustrated in FIG. 9 with the fan detached. Referring to FIGS. 9 and 12, the fan 16 is rotatable in the forward and reverse directions. When the fan 16 is rotated in the forward direction, air in the cabinet 11 is discharged to the outside of the cabinet 11 through the fan 16. When the fan 16 is rotated in the reverse direction, air is introduced from the outside of the cabinet 11 into the cabinet 11 through the fan 16.

The fan 16 is attached to the side surface 11n of the cabinet 11. An opening 120 is formed at a position of the cabinet 11 where the fan 16 is attached. The opening 120 is opened so as to include a region opposite the collection barrel 15 (region indicated by a two-dot chain line 122 in FIG. 12) and a region opposite a brush 51 (region indicated by a two-dot chain line 121 in FIG. 12). The brush 51 will be described later. In the opening 120, the region opposite the collection barrel 15 and the region opposite the brush 51 are continuous with each other.

With this structure, the fan 16 is used in the collecting step, for cooling in the heating step, and in the refreshing step. Thus, the size and the cost of the particle detector 10 can be reduced.

Referring to FIGS. 8 to 11, the collection unit 20 performs the collecting step having been described with reference to FIG. 2, thereby collecting particles suspended in the air onto the collection substrate 71. The collection unit 20 includes a high-voltage power source 21 serving as a power unit and the electrostatic stylus 22 serving as a discharge electrode.

The collection substrate 71 serves as a collection member. Mixed particles of biological particles and dust such as lint of chemical fiber are collected onto the collection substrate 71. The collection substrate 71 is formed of a glass plate. An electrically conductive transparent film is formed on a surface of the glass plate that attracts the particles. The collection substrate 71 is not necessarily formed of a glass plate and may be formed of ceramic, metal, or the like. The film is not necessarily transparent. For example, a metal film may be formed on the surface of the collection substrate 71 formed of ceramic or the like. When the collection substrate 71 is formed of metal, the film is not necessarily formed on the surface of the collection substrate 71.

The high-voltage power source 21 is the power unit used to generate a potential difference between the collection substrate 71 and the electrostatic stylus 22.

The electrostatic stylus 22 extends from the high-voltage power source 21, penetrates through the collection barrel 15, and reaches the inside of the collection barrel 15. In the collecting step, the collection substrate 71 opposes the electrostatic stylus 22. In the present embodiments, the electrostatic stylus 22 is electrically connected to a positive electrode of the high-voltage power source 21. The film formed on the collection substrate 71 is electrically connected to a negative electrode of the high-voltage power source 21.

In the case where the electrostatic stylus 22 is electrically connected to the positive electrode of the high-voltage power source 21, the film formed on the collection substrate 71 may be connected to a ground potential. Alternatively, the electrostatic stylus 22 may be electrically connected to the negative electrode of the high-voltage power source 21 and the film formed on the collection substrate 71 may be electrically connected to the positive electrode of the high-voltage power source 21.

In the collecting step, when the fan 16 is rotated in the forward direction, air in the cabinet 11 is discharged and, at the same time, air outside the cabinet 11 is introduced toward the collection substrate 71 through the collection barrel 15. In so doing, by generating the potential difference between the electrostatic stylus 22 and the collection substrate 71 by using the high-voltage power source 21, airborne particles around the electrostatic stylus 22 are positively charged. The positively charged particles are moved to the collection substrate 71 by electrostatic forces and attracted to the electrically conductive film, thereby being collected onto the collection substrate 71.

As described above, in the particle detector 10 according to the present embodiments, the particles are collected onto the collection substrate 71 by electrostatic collection that utilizes electrostatic forces. In this case, the particles can be reliably held on the collection substrate 71 during detection of the particles, and after the particles have been detected, the particles can be easily removed from the collection substrate 71.

By using the needle-shaped electrostatic stylus 22 as the discharge electrode, the charged particles can be attracted to a very narrow region of the surface of the collection substrate 71 opposite the electrostatic stylus 22, the region corresponding to a region irradiated with the light emitting element, which will be described later. Thus, in the fluorescence measuring step, microorganisms having been attracted can be efficiently detected.

The fluorescence detection unit 30 performs the fluorescence measuring steps (before and after heating) having been described with reference to FIGS. 3 and 5. The fluorescence detection unit 30 includes an excitation light source unit 31 and a light receiving unit 41. The excitation light source unit 31 radiates excitation light toward the particles collected on the collection substrate 71. The light receiving unit 41 receives fluorescence emitted from the particles as the particles are irradiated with the excitation light.

The excitation light source unit 31 includes a light emitting element 32 serving as a light source, an excitation unit frame 33, a condensing lens 34, and a lens pressing member 35. The light receiving unit 41 includes a noise shield 42, an amplification circuit 43, a light receiving element 44, a light receiving unit frame 45, a Fresnel lens 46, and a lens pressing member 47. The light emitting element 32 uses, for example, a semiconductor laser or an LED (light emitting diode) element. The wavelength of light emitted from the light emitting element 32 may be in an ultraviolet range or a visible range as long as the light can excite biological particles and cause the biological particles to emit fluorescent. The light receiving element 44 uses, for example, a photodiode or an image sensor.

The cleaning unit 50 performs the refreshing step having been described with reference to FIG. 6, thereby removing the particles from the collection substrate 71. The cleaning unit 50 includes the brush 51 functioning as a cleaning tool, a brush mount portion 52 as a base portion, and a brush pressing plate 53. The cleaning unit 50 is secured to and supported by the high-voltage power source 21. The cleaning unit 50 remains stationary during the refreshing step.

The brush 51 is formed of a fiber assembly. The brush 51 is formed of an electrically conductive fiber assembly. The brush 51 is formed of, for example, a carbon fiber. It is preferable that the wire diameter of the fiber assembly of the brush 51 be from φ0.05 mm to φ0.2 mm.

The brush 51 has free ends 51p and supported ends 51q (see FIG. 11). The supported ends 51q are disposed at end portions opposite to the free ends 51p. The supported end 51q is supported by the brush mount portion 52 and the brush pressing plate 53. The brush 51 hangs down with the supported ends 51q at the top and the free ends 51p at the bottom. The brush 51 is secured and supported within a range in which the collection substrate 71 is movable. By moving the collection substrate 71 while the free ends 51p of the brush 51 are in contact with the surface of the collection substrate 71, the particles are removed from the collection substrate 71.

The particle detector 10 further includes a heater 76 serving as a heating unit and a movement mechanism 60. The heater 76 performs the heating step having been described with reference to FIG. 4, thereby heating the particles collected on the collection substrate 71.

The movement mechanism 60, to which the collection substrate 71 is attached, moves the collection substrate 71 in the collecting step, the fluorescence measuring steps (before and after heating), the refreshing step, and the heating step. The movement mechanism 60 includes a motor holder 61, a rotating motor 62, a motor pressing member 63, and a rotating base 64. The rotating motor 62 serves as a rotatable drive unit. The rotating base 64 serves as an arm unit.

Referring to FIG. 11, an output shaft of the rotating motor 62 is connected to the rotating base 64. As the rotating motor 62 is driven, the rotating base 64 is rotated (in the forward and reverse directions) about a rotational axis 66 illustrated by a phantom line.

The rotating base 64 is formed of a resin material. The rotating base 64 has the following structural portions: a central portion 67 and a substrate supporting portion 68.

The central portion 67 is connected to the output shaft of the rotating motor 62. The central portion 67 is rotatably supported by the cabinet 11 about the rotational axis 66. The collection substrate 71 is attached to the tip of the substrate supporting portion 68. The substrate supporting portion 68 extends from the central portion 67 in the radial direction of the rotational axis 66. Part of the substrate supporting portion 68, the part being a part to which the collection substrate 71 is attached, has a frame shape.

The heater 76 is bonded to the rear surface of the collection substrate 71. The heater 76 is moved together with the collection substrate 71 when the rotating base 64 is rotated.

In the particle detector 10, by rotating the rotating base 64, the collection substrate 71 can be moved to the following positions: that is, a collecting position where the collecting step is performed, a measuring position where the measuring steps are performed, a heating position where the heating step is performed, and a refreshing position where the refreshing step is performed.

When the fluorescence measuring step (after heating) is completed and the collection substrate 71 is moved to the refreshing position, the entire surface of the collection substrate 71 passes through the free ends 51p of the brush 51 so as to be brought into contact with the free ends 51p of the brush 51. Thus, the particles are removed from the collection substrate 71.

Here, the refreshing position refers to a moving range of the collection substrate 71 in which the collection substrate 71 is in contact with the brush 51, which is secured and supported.

First Embodiment

Figure 13:
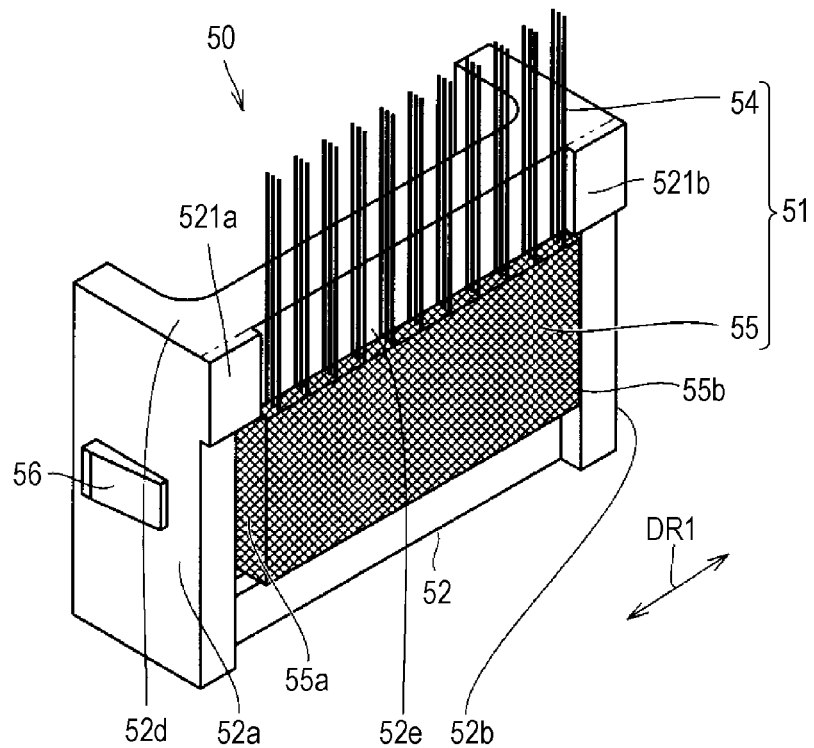
FIG. 13 illustrates the appearance of a cleaning unit according to a first embodiment of the present invention.
Figure 14:
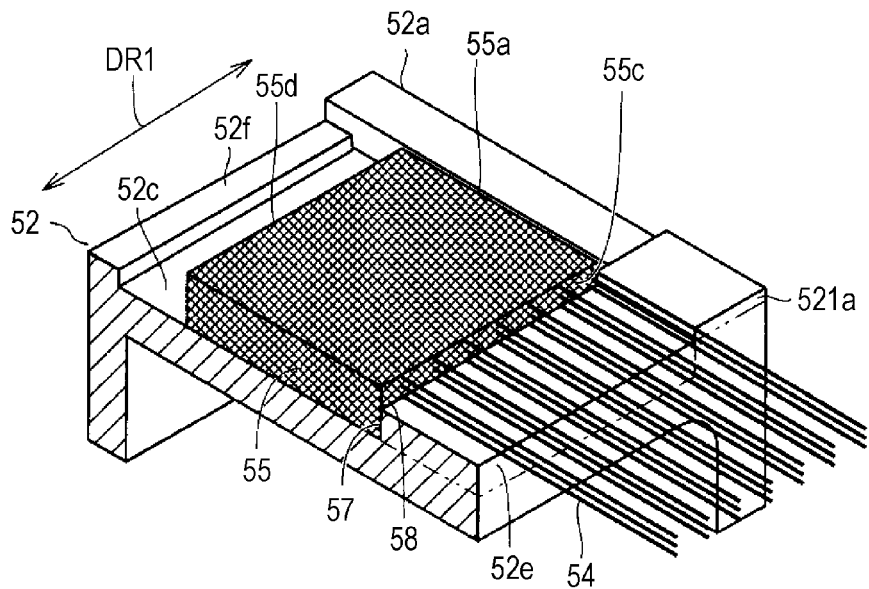
FIG. 14 is a schematic sectional view of the cleaning unit.

FIG. 13 illustrates the appearance of the cleaning unit according to the first embodiment. FIG. 14 is a schematic sectional view of the cleaning unit. Referring to FIGS. 13 and 14, the cleaning unit 50 includes the brush 51 and the brush mount portion 52, to which the brush 51 is secured. The brush 51 includes bristles 54 and a woven portion 55, which is formed by interlacing the roots of the bristles 54 with weaving threads so that the bristles 54 are secured. A plurality of bundles of bristles 54, which each include the plurality of bristles 54, are formed. The plurality of bundles are arranged side by side in a width direction (DR1 direction) of the cleaning unit 50.

The brush mount portion 52 has side walls 52a and 52b, which each have an engagement portion 56, a placement surface 52c, on which the brush 51 is placed, and an upper surface 52d.

The side walls 52a and 52b project further to a front surface side than the placement surface 52c. The woven portion 55 is placed on the placement surface 52c such that the woven portion 55 is disposed in a region between the side walls 52a and 52b. The brush mount portion 52 has a first projecting portion 52e projecting from the placement surface 52c to the front surface side. A step portion 57 is formed between the placement surface 52c and the first projecting portion 52e. A gap is formed between the step portion 57 and the woven portion 55. The gap slows spreading of an adhesive, which will be described later.

The side walls 52a and 52b located at respective ends of the first projecting portion 52e has second projecting portions 521a and 521b, which project further to the front surface side than the first projecting portion 52e. The bristles 54 are disposed so as to be in a region between the second projecting portions 521a and 521b. The bristles 54 are in contact with the first projecting portion 52e of the brush mount portion.

The brush mount portion 52 also has a third projecting portion 52f that projects from the placement surface 52c on a side of the first projecting portion 52e opposite to a side to which the bristles 54 extends. The third projecting portion 52f is disposed between the side walls 52a and 52b. The side walls 52a and 52b project further to the front surface side of the placement surface 52c than the third projecting portion 52f.

The woven portion 55 has first outer surfaces 55a and 55b, which extend parallel to the bristle extending direction, and a second outer surface 55d that opposes an outer surface 55c. The bristles project from the outer surface 55c.

The brush 51 is made by cutting a belt-shaped brush strip. The strip extends in the arrow DR1 direction in FIGS. 13 and 14.

Figure 15:
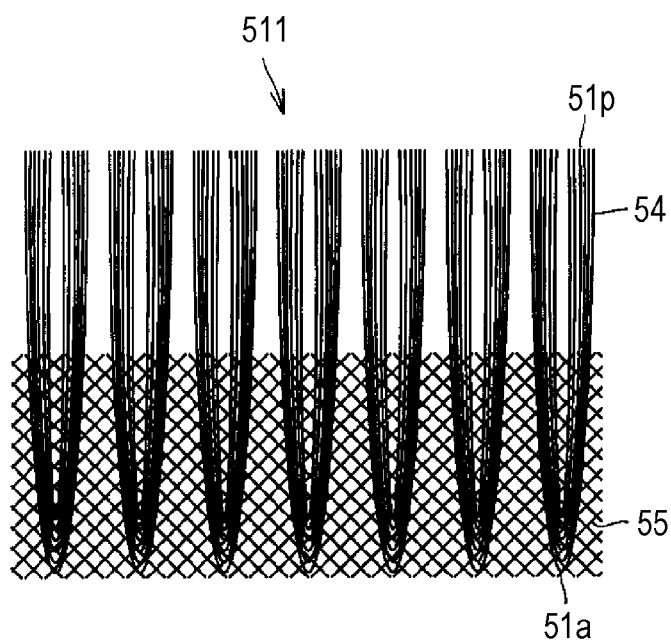
FIG. 15 illustrates a brush strip in the case where bristles are bent.

FIG. 15 illustrates the brush strip in the case where the bristles 54 are bent. Referring to FIG. 15, a strip 511 is woven by interlacing the plurality of arranged bundles of bristles 54 having been bent into a U-shape with the weaving threads that extend in a direction intersecting the bristle 54 extending direction on the root side including bent portions 51a. The bent portions 51a and the free ends 51p are arranged in respective lines extending in a direction substantially perpendicular to the bristle 54 extending direction. The bundles of the bristles 54 are equally spaced apart from one another.

Figure 16:
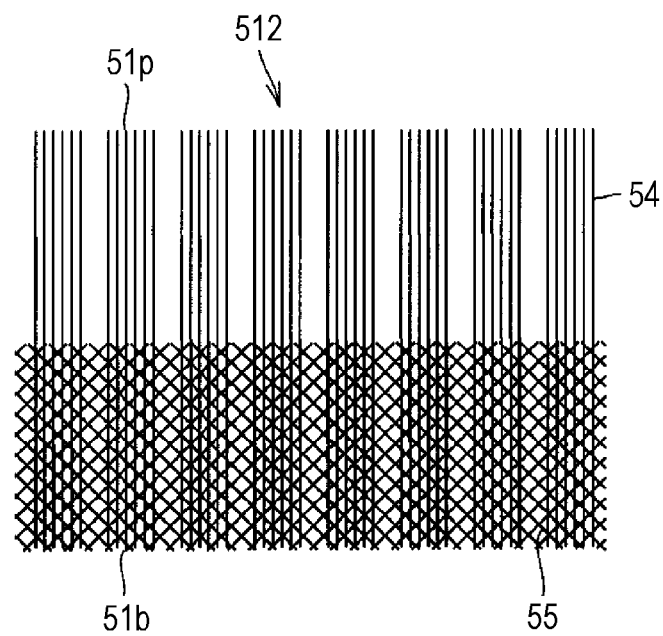
FIG. 16 illustrates the brush strip in the case where the bristles are not bent.

FIG. 16 illustrates the brush strip in the case where the bristles 54 are not bent. Referring to FIG. 16, a strip 512 is woven by interlacing the plurality of arranged bundles of straight bristles 54 with the weaving threads that extend in the direction intersecting the bristle 54 extending direction on the root side (one end side) of the bristles 54. The free ends 51p and end portions 51b of the bristles 54, the end portions 51b being located on a side opposite to the free ends 51p, are arranged in respective lines extending in a direction substantially perpendicular to the bristle 54 extending direction. The bundles of the bristles 54 are equally spaced apart from one another.

The brush strip 511, 512 is sufficiently longer than the collection substrate 71 of the particle detector 10. Thus, when attaching the brush 51 to the brush mount portion 52 to assemble the cleaning unit, the strip 511, 512 needs to be cut. When the brush strip 511, 512, is cut, the bundles of the bristles 54, which are tightly arranged, are likely to be cut at the middle thereof. The strip 511, 512 is cut in a direction substantially parallel to the bristle 54 extending direction, that is, in a direction perpendicular to a direction in which the strip extends.

Figure 17:
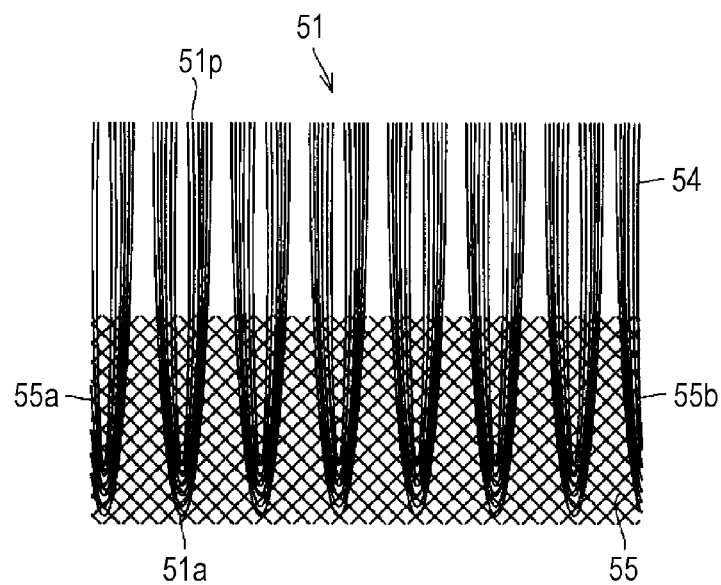
FIG. 17 illustrates a state of a brush cut from the brush strip.

FIG. 17 illustrates a state of the brush cut from the brush strip. Referring to FIG. 17, the brush strip is cut on an outer side of the bent portion 51a on the first outer surface 55a side (left in FIG. 17) of the woven portion 55. The brush strip is also cut on an inner side of the bent portion 51a on a first outer surface 55b side (right in FIG. 17) of the woven portion 55.

In the case where the bundles of the bristles 54 are cut at the middle as described above, weaving threads are cut and become loose on the first outer surfaces 55a and 55b sides of the woven portion 55. Thus, compared to the center of the brush 51 where the bundle is not cut, holding forces by which the bristles 54 woven into the woven portion 55 are held are reduced. Furthermore, when the collection substrate 71 is repeatedly moved so as to be brought into contact with the brush 51, the weaving threads are further loosened, and accordingly, the holding forces are further reduced. Thus, the bristles 54 are likely to be removed on the first outer surfaces 55a and 55b.

When the bristles 54 are removed and attracted to the surface of the collection substrate 71 during drive of the particle detector 10, a voltage for charging the particles cannot be applied between the collection substrate 71 and the electrostatic stylus 22. This degrades collection performance and reduces the stability of measured results. Accordingly, in order to stabilize measured results, it is required that the bristles 54 be prevented from being removed from the brush 51. In the cleaning unit 50 according to the present embodiment, by adjusting locations where an adhesive is applied when the brush mount portion 52 and the brush 51 are bonded to each other, the bristles 54 are prevented from being removed from the brush 51.

Figure 18:
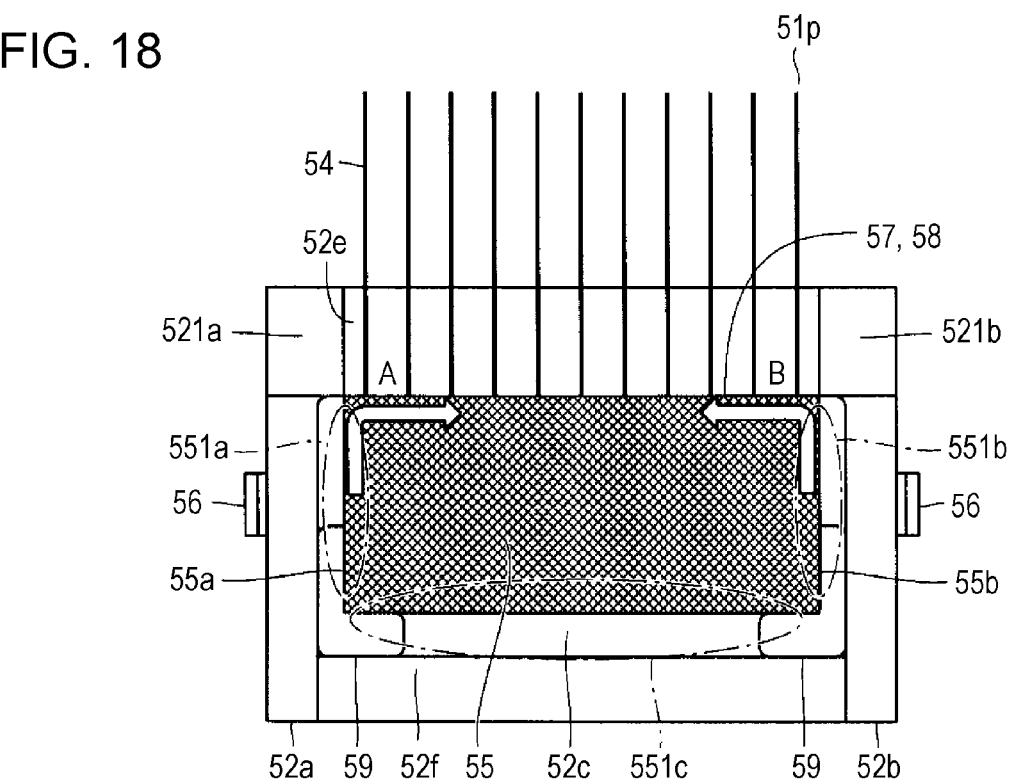
FIG. 18 illustrates locations where an adhesive is applied and spreading of the adhesive.

FIG. 18 illustrates the locations where the adhesive is applied and spreading of the adhesive. Referring to FIG. 18, the adhesive is applied to adhesive application regions 551a and 551b located on the first outer surfaces 55a and 55b sides of the woven portion 55 while the brush 51 is placed on the placement surface 52c of the brush mount portion 52. The adhesive is, for example, a photo-curable resin. The brush 51 is positioned by positioning portions 59 provided in the brush mount portion 52. The positioning portions 59 each have an L shape so as to be in contact with the side walls 52a or 52b and the third projecting portion 52f. The adhesive may alternatively be a heat-curable resin or a photo/heat curable resin.

The adhesive applied to the adhesive application regions 551a and 551b is subjected to UV radiation or the like so as to be cured. Thus, the first outer surfaces 55a and 55b are respectively secured to the side walls 52a and 52b. The holding forces of the first outer surfaces 55a and 55b having been reduced because of cutting of the weaving threads are increased by securing the first outer surfaces 55a and 55b to the side walls 52a and 52b with the adhesive. Furthermore, this can suppress an increase in loosening of the weaving threads occurring due to the repeated movement of the collection substrate 71. Thus, the likelihood of removal of the bristles 54 is reduced even when an external force is applied to the tips of the bristles 54.

Furthermore, the adhesive may be applied to an adhesive application region 551c located on the second outer surface 55c opposite to a side toward which the bristles 54 extend. The adhesive applied to the adhesive application region 551c, when cured, secures the second outer surface 55c to the third projecting portion 52f of the brush mount portion 52. By securing the second outer surface 55d to the third projecting portion 52f, a holding force that holds the weaving threads located in the second outer surface 55d is increased. This can prevent the bristles 54 from being removed from a central portion of the woven portion 55.

However, when the adhesive is used to secure the brush 51, the cleaning function may be lost because the tips (free ends 51p) of the bristles 54 are bonded by the adhesive spreading to the tips of the bristles 54.

Specifically, the brush 51 has very thin bristle materials gathered together therein. Thus, the adhesive spreads toward the tips of the bristles 54 due to capillary action until the adhesive is cured by light such as UV radiated thereto. When the adhesive having spread to the tips of the bristles 54 is cured, the bristles 54 are secured and become immovable. Thus, the collection substrate 71 cannot be cleaned. Accordingly, it is required that the spreading of the adhesive be suppressed so as to maintain the cleaning function of the brush.

In the cleaning unit 50 according to the present embodiment, the step portion 57 is formed between the placement surface 52c and the first projecting portion 52e as described above. Thus, the adhesive having been applied to the adhesive application regions 551a and 551b and spread in the woven portion 55 is brought into contact with the step portion 57. This changes an advancing direction of the adhesive to directions toward the central portion as indicated by arrows A and B. The adhesive in the changed advancing directions spreads the woven portion 55 to the central portion. Thus, the spreading of the adhesive to the tips of the bristles 54 can be suppressed.

When a gap 58 is formed between the step portion 57 and the woven portion 55 (this gap is optional), the adhesive can be retained in the gap 58. Thus, the spreading of the adhesive to the tip side of the bristles 54 can be suppressed until the gap 58 is filled with the adhesive.

Thus, by suppressing the spreading of the adhesive, a time period required to cure the adhesive with the UV can be obtained. As a result, the tips of the bristles 54 can be prevented from being bonded to one another.

In this case, bonding portions where the brush 51 and the brush mount portion 52 are bonded to each other are the side walls 52a and 52b and part of the placement surface 52c to which the adhesive has spread.

Next, the cleaning function is described. Since the adhesive is stopped by the step portion 57 or the gap 58, leading end positions of the adhesive that suppresses the movement of the bristles 54 are determined at a position of the step portion 57 or the gap 58. Parts of the bristles 54 between the leading end positions of the adhesive to the free ends 51p can move and clean the collection substrate 71. The free ends 51p of the bristles 54 are arranged in the line substantially perpendicular to a direction in which the brush extends. Thus, the distances between the leading end positions of the adhesive adhering to the plurality of bristles 54 and the free ends 51p are uniform. Thus, the collection substrate 71 can be uniformly cleaned.

However, when the adhesive is not stopped by the gap 58 between the step portion 57 and the woven portion 55, part of the adhesive spreads to the first projecting portion 52e. In this case, the spreading of the adhesive toward the free ends 51p of the bristles 54 is not uniform. Thus, when the adhesive is cured, the distances between the leading end positions of the adhesive to the free ends 51p are not uniform among the bristles 54. As a result, it is difficult to uniformly clean the collection substrate 71. In this case, bonding portions where the brush 51 and the brush mount portion 52 are bonded to each other are the side walls 52a and 52b, part of the placement surface 52c to which the adhesive has spread, and part of the first projecting portion 52e.

In the cleaning unit 50 according to the present embodiment, the bristles 54 are also secured by the brush pressing plate 53. Thus, the collection substrate 71 can be uniformly cleaned.

Figure 19:
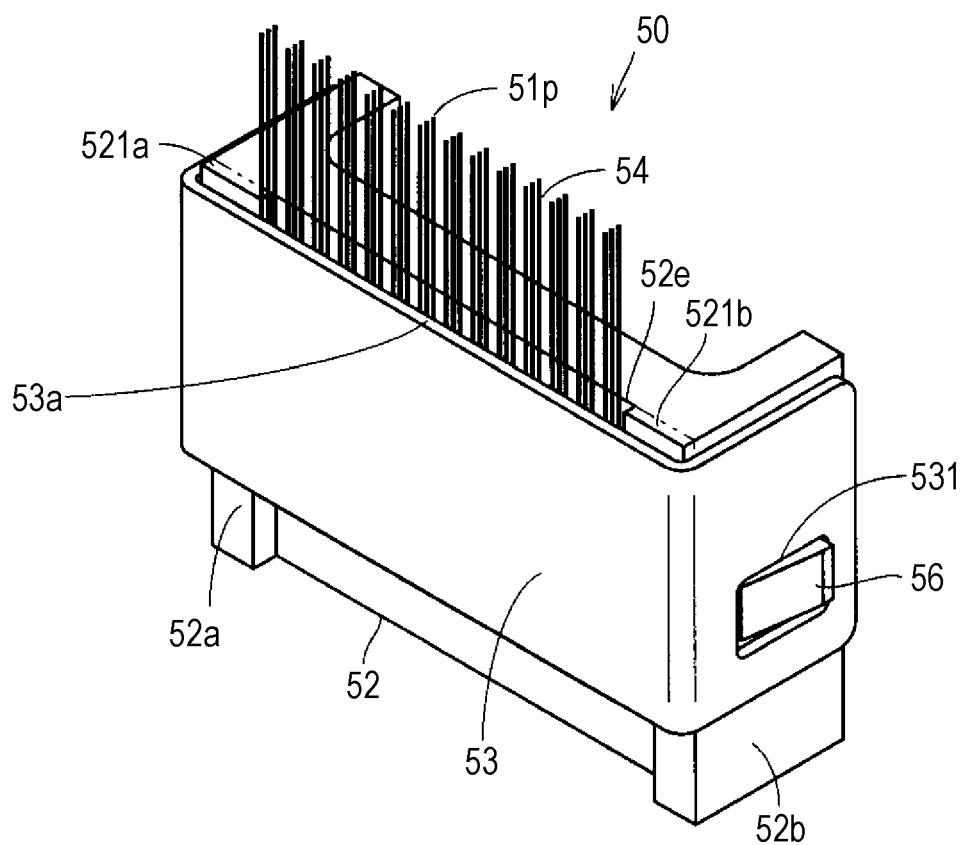
FIG. 19 illustrates a state in which the brush is secured with the brush pressing plate.

FIG. 19 illustrates the brush secured by the brush pressing plate. Referring to FIG. 19, the brush pressing plate 53 is disposed such that the brush pressing plate 53 opposes the first projecting portion 52e and the above-described bonding portions of the brush mount portion 52 so as to pinch the brush 51 to secure the brush 51. The brush pressing plate 53 is engaged with the brush mount portion 52 through the engagement portions 56.

The brush pressing plate 53 has openings 531 engaged with the engagement portions 56 provided on the side walls 52a and 52b of the brush mount portion 52. The brush pressing plate 53 is in contact with the second projecting portions 521a and 521b of the brush mount portion 52 and presses the bristles 54 at securing positions 53a to secure the bristles 54.

Thus, the position where the movement of the brush is suppressed is moved from the leading end positions of the adhesive having spread to part of the first projecting portion to the securing positions 53a where the brush pressing plate 53 pushes the bristles 54. As a result, bristles 54 projecting from the brush pressing plate 53 have the function of cleaning the collection substrate 71.

Since the securing positions 53a where the brush pressing plate 53 secures the bristles 54 are arranged in a line substantially perpendicular to the brush extending direction, the distances between the securing positions 53a where the movement of the bristles 54 is suppressed to the free ends 51p of the bristles 54 are uniform among the plurality of the bristles 54. Thus, the collection substrate 71 can be uniformly cleaned. Since the bristles 54 are pinched between the brush pressing plate 53 and the first projecting portion 52e, spreading of the bristles 54 occurring due to iterative cleaning in the particle detector can be suppressed.

Figure 20:
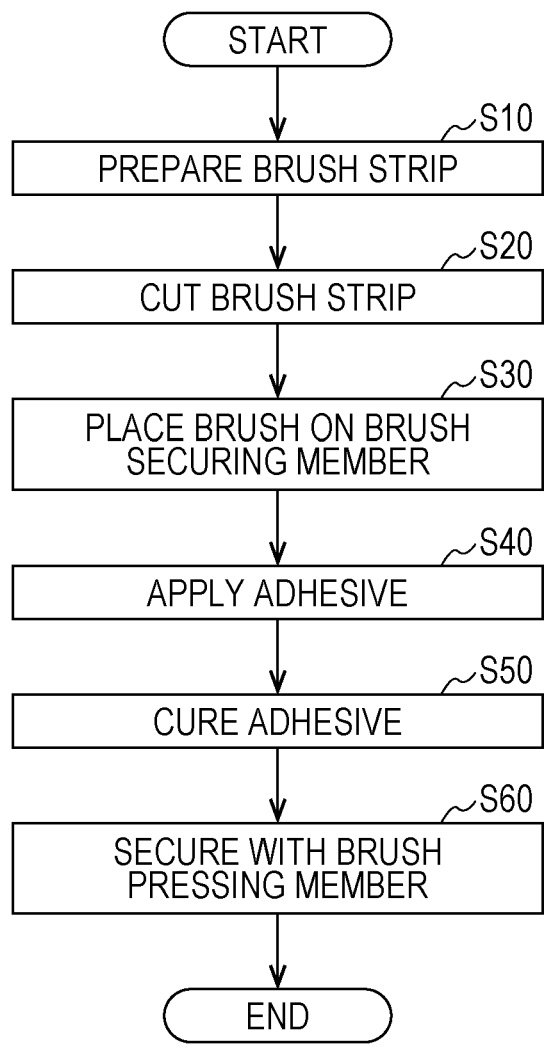
FIG. 20 is a flowchart illustrating a flow of manufacturing the cleaning unit.

FIG. 20 is a flowchart illustrating a flow of manufacturing the cleaning unit according to the present embodiment. Referring to FIG. 20, the brush strip is prepared. The brush strip includes the bristles 54 and the woven portion formed by interlacing the roots of the bristles 54 with the weaving threads so that the bristles 54 are secured (step S10).

Next, the brush strip is cut in a direction perpendicular to a direction in which the strip extends so as to cut off the brush 51 having a width sufficient to clean the collection substrate 71 (step S20). The brush 51 having been cut off is placed on the placement surface 52c of the brush mount portion 52 (step S30). In so doing, the brush 51 is placed such that the brush 51 is disposed between the side walls 52a and 52b of the brush mount portion 52 and positioned with the positioning portions 59. Furthermore, the brush 51 is placed such that the gap 58 is formed between the brush 51 and the first projecting portion 52e of the brush mount portion 52. The bristles 54 are arranged between the second projecting portions 521a and 521b located at both the ends of the first projecting portion 52e.

Next, the adhesive is applied to the first outer surfaces 55a and 55b sides of the woven portion 55 (step S40). In so doing, directions of the flows of the adhesive are changed to those toward the center of the brush mount portion 52 by the step portion 57 between the first projecting portion 52e and the placement surface 52c of the brush mount portion 52. This suppresses the spreading of the adhesive to the tips of the bristles 54. Also, the spreading of the adhesive to the bristles 54 is suppressed until the gap 58 is filled with the adhesive continues. Steps S30 and S40 may be performed in a reverse order.

After that, the adhesive having been applied is irradiated with the UV so as to be cured (step S50). Then, the brush pressing plate 53 is disposed such that the brush pressing plate 53 opposes the first projecting portion 52e and the above-described bonding portion of the brush mount portion 52 so as to pinch the brush 51 to secure the brush 51 (step S60). With the brush pressing plate 53, the positions where the movement of the plurality of bristles 54 are suppressed are uniformly set. Thus, the distances between the securing positions 53a of the bristles 54 and the free ends 51p of the bristles 54 can be equalized. As a result, the collection substrate 71 can be uniformly cleaned.

Second Embodiment

Figure 21:
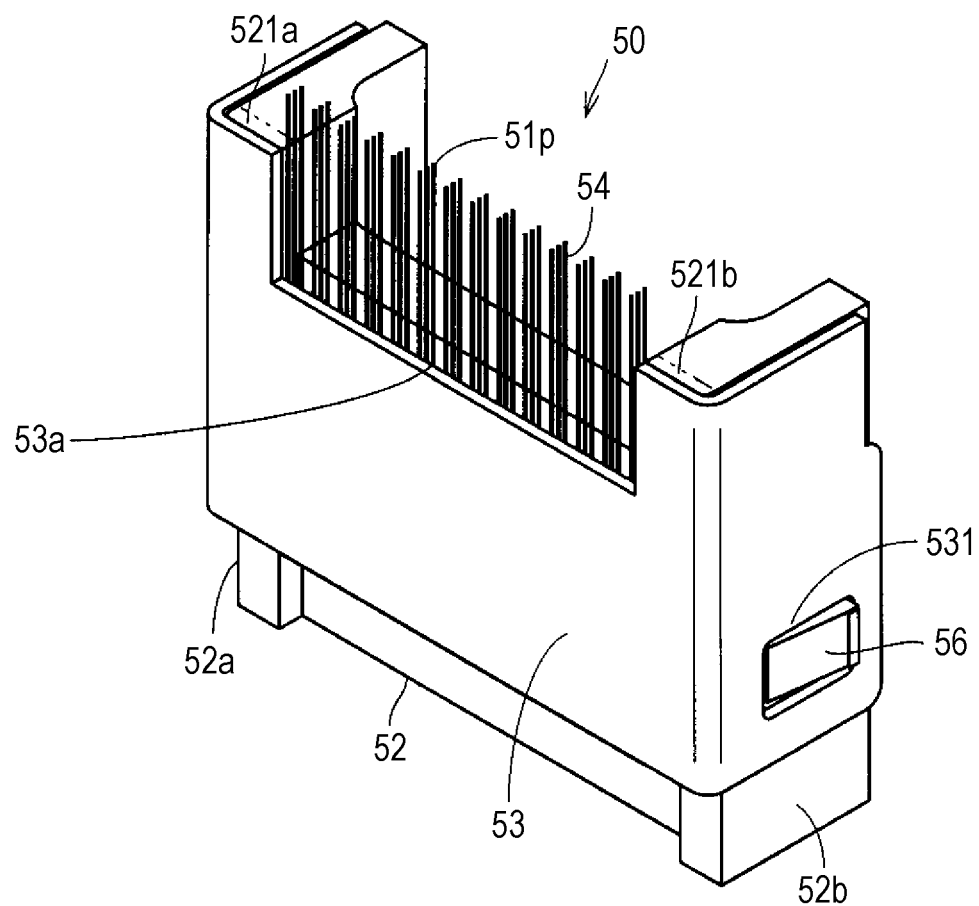
FIG. 21 illustrates the appearance of a cleaning unit according to a second embodiment of the present invention.

FIG. 21 illustrates the cleaning unit according to a second embodiment. The cleaning unit according to the second embodiment is different from the cleaning unit according to the first embodiment as follows: that is, the side walls 52a and 52b and the second projecting portions 521a and 521b of the brush mount portion 52 are enlarged so as to extend further in the bristles 54 extending direction.

By enlarging the second projecting portions 521a and 521b, the area in which the brush pressing plate 53 is in contact with the brush mount portion 52 is increased. When the area in which the brush pressing plate 53 is in contact with the brush mount portion 52 is increased, the bristles 54 are secured more firmly than with the cleaning unit according to the first embodiment. Thus, the spreading of the bristles 54 occurring due to iterative cleaning in the particle detector can be further suppressed.

Although the embodiments of the present invention have been described, it should be understood that the embodiments disclosed herein are exemplary and not limiting in any sense. It is intended that the scope of the present invention is defined by the scope of the claims, and any modification within the meaning and the scope equivalent to the scope of the claims is included in the scope of the present invention.

10 particle detector, 11 cabinet, 11m, 11n side surface, 12 upper cabinet, 14 lower cabinet, 15 collection barrel, 16 fan, 19 projecting portion, 20 collection unit, 21 high-voltage power source, 22 electrostatic stylus, 30 fluorescence detection unit, 31 excitation light source unit, 32 light emitting element, 33 excitation unit frame, 34 condensing lens, 41 light receiving unit, 42 noise shield, 43 amplification circuit, 44 light receiving element, 45 light receiving unit frame, 46 Fresnel lens, 50 cleaning unit, 51 brush, 51a bent portion, 51b end portion, 51p free end, 51q supported end, 52 brush mount portion, 52a, 52b side wall, 52c placement surface, 52d upper surface, 52e first projecting portion, 52f third projecting portion, 53 brush pressing plate, 53a securing position, 54 bristle, 55 woven portion, 55a, 55b first outer surface, 55d second outer surface, 56 engagement portion, 57 step portion, 58 gap, 59 positioning portion, 60 movement mechanism, 61 motor holder, rotating motor, 64 rotating base, 66 rotational axis, 67 central portion, 68 substrate supporting portion, 71 collection substrate, 76 heater, 91 collection/heating position, 92 detection position, 93 refreshing position, 120, 531 opening, 511, 512 strip, 521a, 521b second projecting portion, 551a, 551b, 551c adhesive application region.

The invention claimed is:

1. A cleaning tool for a collection member that cleans a collection member of a particle detector, the tool comprising:
    a brush unit that includes a bristle and a woven portion into which a root of the bristle is woven so as to be held by the woven portion; and
    a mount portion that includes
        a placement surface on which the woven portion is placed, and
        a securing portion to which the brush unit is bonded,
    wherein the woven portion includes two first outer surfaces that are located at respective ends of the placement surface and that extend parallel to a direction in which the bristle extends, and
    wherein the brush unit is secured to the mount portion by bonding a region that includes at least part of each of the two first outer surfaces to the securing portion with an adhesive.

2. The cleaning tool for the collection member according to claim 1,
    wherein the mount portion includes
        a bonding portion that includes the placement surface, and
        a first projecting portion that projects from the placement surface and that is in contact with the bristle, and
    wherein a step is formed between the bonding portion and the first projecting portion.

3. The cleaning tool for the collection member according to claim 2,
    wherein a gap is formed between the first projecting portion and the woven portion.

4. The cleaning tool for the collection member according to claim 2, further comprising:
    a pressing plate that opposes the bonding portion and the first projecting portion, the pressing plate together with the mount portion pinching the brush unit.

5. The cleaning tool for the collection member according to claim 4,
    wherein the mount portion further includes second projecting portions that project further to the bristle side than the first projecting portion at both ends of the first projecting portion and that are in contact with the pressing plate.

6. A particle detector comprising:
the cleaning tool for the collection member according to claim 1.

7. The particle detector according claim 6,
wherein, after heating of the collection member has been performed, the collection member is cleaned by the brush unit.

8. The cleaning tool for the collection member according to claim 1,
wherein the woven portion further includes a second outer surface that opposes an outer surface from which the bristle projects, and
wherein, in addition to the two first outer surfaces, the second outer surface is bonded to the securing portion.

* * * * *